(12) United States Patent
Goyarts (10) Patent No.: US 8,057,885 B2
(45) Date of Patent: Nov. 15, 2011

(54) WASHABLE UNDERPAD AND METHOD FOR PRODUCING AN UNDERPAD OF THIS TYPE

(75) Inventor: Gregorius Maria Hubertus Goyarts, Oisterwijk (NL)

(73) Assignee: MIP Inc., Anjou, Quebec (CA)

( * ) Notice: Subject to any disclaimer, the term of this patent is extended or adjusted under 35 U.S.C. 154(b) by 754 days.

(21) Appl. No.: 10/551,781

(22) PCT Filed: Apr. 2, 2004

(86) PCT No.: PCT/NL2004/000221
§ 371 (c)(1),
(2), (4) Date: Oct. 5, 2005

(87) PCT Pub. No.: WO2004/089267
PCT Pub. Date: Oct. 21, 2004

(65) Prior Publication Data
US 2006/0198993 A1    Sep. 7, 2006

(30) Foreign Application Priority Data
Apr. 10, 2003 (NL) .................................... 1023144

(51) Int. Cl.
*B32B 3/00* (2006.01)
*B05D 7/24* (2006.01)

(52) U.S. Cl. ........ 428/198; 428/197; 442/288; 427/210; 427/208.2; 264/157

(58) Field of Classification Search ................ 156/291; 428/198, 201; 5/484, 500, 502; 427/210, 427/208.2; 442/288; 264/157
See application file for complete search history.

(56) References Cited

U.S. PATENT DOCUMENTS
4,045,833 A  *  9/1977   Mesek et al. ..................... 5/484
(Continued)

FOREIGN PATENT DOCUMENTS
CA        2413921 A1    5/2000
(Continued)

OTHER PUBLICATIONS

Dow Chemical Extrusion Coating, "Plastics Asia-Pacific Home: Fabrication Processes: Extrusion Coating/Lamination"; http://plastics.dow.com/plastics/ap/fab/extrusion.htm; pp. 1 and 2; The Dow Chemical Company, 1995-2006.

(Continued)

*Primary Examiner* — Callie Shosho
*Assistant Examiner* — Prashant J Khatri
(74) *Attorney, Agent, or Firm* — Ryan A. Schneider, Esq.; Troutman Sanders LLP (57) ABSTRACT

The invention relates to a multilayer washable material which comprises at least one layer of a textile material, the layers being joined to one another using an adhesive composition, which is characterized in that in the interfacial region between each pair of layers bearing against one another there is an adhesive composition in the form of a pattern, and no finishing of the multilayer material, as such and/or of a smaller part obtained therefrom, is carried out. One example of a multilayer washable material of this type is a washable underpad comprising a moisture-permeable top layer material (2); a moisture-impermeable bottom layer material (3) and a moisture-absorption element (1) positioned between them, the top layer material (2), the bottom layer material (3) and the moisture-absorption element (1) being joined to one another. The adhesive composition used is preferably a moisture-curing reactive polyurethane hotmelt material.

21 Claims, 5 Drawing Sheets

U.S. PATENT DOCUMENTS

| | | | |
|---|---|---|---|
| 4,097,943 A | 7/1978 | O'Connell | |
| 4,216,774 A | 8/1980 | Graber | |
| 4,551,144 A | 11/1985 | Graber | |
| 4,650,481 A | 3/1987 | O'Connor et al. | |
| 4,911,948 A * | 3/1990 | McIntyre | 427/591 |
| 4,961,982 A | 10/1990 | Taylor | |
| 4,978,566 A | 12/1990 | Scheurer et al. | |
| 5,085,653 A | 2/1992 | Levy | |
| 5,087,253 A | 2/1992 | Cooper | |
| 5,114,418 A * | 5/1992 | Levy | 604/365 |
| 5,249,320 A | 10/1993 | Moretz et al. | |
| 5,252,374 A | 10/1993 | Larsonneur | |
| 5,306,267 A | 4/1994 | Hahn et al. | |
| 5,330,817 A | 7/1994 | Arnott et al. | |
| 5,562,648 A * | 10/1996 | Peterson | 604/370 |
| 5,599,339 A | 2/1997 | Horney | |
| 5,662,991 A * | 9/1997 | Smolik et al. | 442/319 |
| 5,938,162 A | 8/1999 | Honjo | |
| 6,127,595 A | 10/2000 | Makoui et al. | |
| 6,245,693 B1 * | 6/2001 | Gagliardi et al. | 442/76 |
| 6,774,067 B2 | 8/2004 | Demott et al. | |
| 2001/0001300 A1 | 5/2001 | Tolbert et al. | |
| 2002/0141898 A1 * | 10/2002 | Carlucci et al. | 422/5 |

FOREIGN PATENT DOCUMENTS

| | | |
|---|---|---|
| DE | 3635339 | 4/1988 |
| EP | 0211815 | 2/1987 |
| EP | 0211815 A | 2/1987 |
| EP | 0331215 | 9/1989 |
| GB | 1404453 | 8/1975 |
| GB | 1404453 A | 8/1975 |

OTHER PUBLICATIONS

H.B. Fuller, "Global Adhesives: Textile"; http://www.hbfulleradhesives.com/industries/textiles/index.shtml; p. 1; 2006.

H.B. Fuller GmbH, Brochure Ipathennm S 14/80, 1987.

Kirk-Othmer "Encyclopedia of Chemical Technology," Fourth Edition; vol. 1; A Wiley-Interscience Publication; pp. 445-466; 1991.

Brochure for "Reactive Hot Melts: The Textile Market,"; 2002.

International Search Report of PCT/NL2004/000221, dated Aug. 4, 2004.

NL Search Report of NL 1023144, dated Apr. 1, 2003.

Canadian Office Action in CA2562311, a related case to U.S. Appl. No. 10/551,781 dated Dec. 9, 2010.

* cited by examiner

WASHABLE UNDERPAD AND METHOD FOR PRODUCING AN UNDERPAD OF THIS TYPE

BENEFIT CLAIMS

This application is a US National Stage of International Application No. PCT/NL2004/00221 filed 2 Apr. 2004, which claims the benefit of NL 1023144, filed 10 Apr. 2003.

The invention relates firstly to a multilayer washable material which comprises at least one layer of a textile material and in which the layers are joined to one another by means of an adhesive composition.

A material of this type is known from US2001/0001300.

The said US application describes a washable textile item and a method for producing it in which layers of textile material are joined to one another by means of a simulated stitching pattern which is formed from a curable hotmelt adhesive which is applied in the molten form. The layers are placed against one another and the adhesive penetrates into the fibre structure of the layers as a result of the application of pressure, so that after curing of the adhesive the layers are joined to one another.

A known material of this type has the drawback that the way in which the various layers are joined adopts a stitching pattern character, with the result that wrinkles may occur during use. If a multilayer material of this type is used, for example, as a washable incontinence underpad, the patient may find wrinkles of this nature very unpleasant and even painful and/or harmful.

It is an object of the present invention to provide an improved washable multilayer material of the abovementioned type in which at least wrinkling can no longer occur, and to this end is characterized in that in the interfacial region between each pair of layers bearing against one another there is an adhesive composition in the form of a pattern which prevents wrinkling, and no finishing of the multilayer material, as such and/or of a smaller part obtained therefrom, is carried out.

The term in the form of a pattern which prevents wrinkling in this context is to be understood as meaning a pattern shape which on the one hand has a density of joining locations between the layers which is such that wrinkling can only occur at a micro-level and is not considered a problem by the user, yet on the other hand, the total bonded area is sufficiently small for the multilayer material to be extremely flexible in use. The following text will explain examples of such patterns.

Where the above text refers to finishing, this will often be understood as meaning edge finishing. However, it should be emphasized that the stitching work which is known from the prior art and is used to fix the various layers with respect to one another is also eliminated. Therefore, the elimination of finishing is to be understood in a broad sense; the only work which is carried out if required in order to obtain a multilayer, ready-to-use material of the desired format is a cutting, trimming or stamping operation. As an example of a multilayer washable material according to the invention, it is possible to think of underpad material as mentioned above; mention may also be made of bandages, wound-covering material, stoma attachment material, dressing material, pantyliners, sanitary towels and many others. The multilayer washable material is expediently a material comprising three layers, in which case, by way of example, an absorption body is surrounded by covering layers selected from moisture-permeable and moisture-impermeable material. If one of the layers is to be moisture-impermeable, this material may, for example, be a moisture-impermeable plastic material, such as polyurethane, polyethylene and the like.

Another multilayer material may, for example, comprise three layers with the top layer material and bottom layer material being identical. A material of this type can be used on both sides, making it very easy to use for the user.

The washable material, on account of the way in which the layers have been joined in a pattern shape, is sufficiently cohesive to allow it to be used as such without any finishing after it has been cut or trimmed into any desired pattern and to allow it to be reused, after washing, without any significant fraying or loss of cohesion occurring over the course of time.

As has already been indicated, the pattern shape which prevents wrinkling may be in a wide range of forms, and is expediently selected from:
a) a dot lining pattern,
b) separately positioned pattern parts which are separated by regions where there is no adhesive composition,
c) a number of pattern parts which are identical in shape and one or more pattern parts of a different shape,
d) the patterns described under b) and/or c), with one or more pattern parts being formed from a dot lining pattern,
e) a dot lining pattern as described under a) in which there are parts without any dots,
and combinations of the patterns described under a) to e).

The number of possible pattern shapes that can be used is not limited to those indicated above; many other options will be obvious to the person skilled in the art on reading the present description. Any pattern which is sufficiently dense to prevent wrinkling and at the same time is sufficiently open (i.e. has a sufficient surface area without any adhesive) to prevent the material from becoming inflexible is suitable for use in the present materials.

In particular, the invention relates to a washable underpad comprising a moisture-permeable top layer material; a moisture-impermeable bottom layer material and a moisture-absorption element positioned between them, the top layer material, the bottom layer material and the moisture-absorption element being joined to one another.

In the context of the present invention, the term underpad is to be understood as meaning on the one hand a ready-to-use underpad as such which can be used directly to provide comfort to a bedridden incontinent patient and to protect the mattress on which the patient is lying.

On the other hand, the underpad may also be a material from which it is possible to make one or more underpads or other objects in which the function of the material is of benefit.

Whereas the prior art often required joining by stitching or the like in order to join the various layers to one another in such a manner that there was no separation of the layers during washing of the underpad, the Applicant has now discovered that by using adhesives it is possible to join the top layer material and the bottom layer material to the moisture-absorption element in such a manner that the underpad has an excellent long-term washability without separation of the layers occurring. By suitably selecting the pattern shape of the adhesive composition, it is possible to effectively prevent wrinkling in the plane of the underpad.

The moisture-permeable top layer material for an underpad can be selected from numerous materials which have a good moisture-permeability and are substantially hydrophobic. The top layer material is, for example, expediently a knitted material which comprises fibres selected from polyester, polyamide and polyethylene or mixtures thereof. It is also possible to use mixtures of synthetic and natural fibres, such as polyester/cotton, for example in a ratio from 80% polyester/20% cotton to 50% polyester/50% cotton.

In certain cases, if the absorption element has an extremely high absorption capacity, the top layer material may even be made from 100% cotton. In particular, a suitable top layer material is a knitted polyester material which is raised on the side which comes into contact with the patient, so that a soft surface is obtained. It is also possible to use a towelling layer or a dryness layer, in particular if the underpad is provided with a non-fraying edge, as explained below.

A moisture-absorption element which can be used in the washable underpad according to the invention is expediently an assembly of chemical fibres, such as viscose or modified viscose and synthetic fibres selected from polyester, polyamide, polyacrylate, polypropylene and the like; a moisture-absorption element of this type is described in the Applicant's The term "chemical fibres" relates to a fibre which is based on a natural product, such as cellulose, and which has been converted into a form which is suitable for human use by means of a chemical treatment. A synthetic fibre is a fibre produced from a polymer which is produced entirely by chemical synthesis without any natural product base being present.

The moisture-absorption element expediently comprises, for example, 90 to 10% chemical fibres, such as viscose or modified viscose, and 10 to 90% synthetic fibres, such as polyester, polyamide, polyacrylate, polypropylene and the like.

The moisture-absorption element expediently comprises 10 to 40% chemical fibres and 90 to 60% synthetic fibres, and the moisture-absorption element is preferably composed of 70% polyester and 30% viscose, more preferably 85% polyester and 15% viscose, with needling having been carried out in order to obtain optimum bonding between the fibres. The needling of the fibre mixture results in a cohesion which is such that the moisture-absorption element can withstand numerous washes without problems.

If desired, the moisture-absorption element may, in order to accelerate its drying after it has been washed, comprise perforations which extend over at least part of the height of the moisture-absorption element. It is expedient for the perforations to extend over the entire height of the moisture-absorption element. The perforations generally have a diameter of from 1 to 5 mm and a centre-to-centre distance of from 8 to 30 mm. In particular, the perforations have a diameter of approximately 3 mm and a centre-to-centre distance of approximately 12 mm.

In the absorption element, the chemical fibres, such as viscose or modified viscose generally have a thickness of from 1 to 8 dTex and a length of from 30 to 100 mm, while the synthetic fibres, such as polyester, comprise fibres with a thickness of from 1 to 10 dTex and a length of from 30 to 100 mm. The synthetic fibres, such as polyester, may expediently comprise additional polyester with a thickness of less than 1 dTex and a length of from 30 to 80 mm.

It is expedient to use a mixture of chemical fibres and synthetic fibres in the moisture-absorption element, as has been explained above. However, it has been found that moisture-absorption elements which consist entirely of synthetic fibres can also be used with success. Tests using moisture-absorption elements consisting entirely of polyester fibres were very successful. Advantages obtained included, inter alia, mechanical stability, washability (no residual soiling on account of the absence of absorption in the fibre), hygiene, bonding to the adhesive compositions.

The moisture-impermeable bottom layer material may be any suitable plastic material, such as polyvinyl chloride, polyethylene, polyurethane and any other synthetic, moisture-impermeable material. The material may be thermoplastic or non-thermoplastic and must not, of course, have any adverse effect on the skin of the patient using it.

The bottom layer material may be a textile material which is coated with a plastic material.

It is also possible for a textile material to be coated with a plastic film, such as PVC or PU by laminating or adhesive bonding and then to be used as the bottom layer material.

In a highly attractive embodiment, the bottom layer material may comprise a non-slip layer in the form of a coating in pattern form on the side which faces away from the absorption body. The pattern shape may comprise any of the shapes described above, but is expediently a dot pattern. A non-slip pattern of this type prevents, for example, an underpad from slipping with respect to the mattress on which it rests. Suitable materials for a dot pattern of this type include the conventional rubber-like plastic materials, such as PU, PVC and synthetic rubber; the dot pattern is expediently formed by printing the bottom layer material using screen printing followed by drying/curing of the dot coating layer which has been applied.

In general, of course, the materials should be selected such that bonding is produced between the various layers of the washable multilayer material with the aid of the adhesives used in the invention.

It is expedient for the adhesive used in each of the interfacial regions referred to above to be employed in a pattern shape. Obviously, it should be ensured that moisture can pass freely from the top layer material to the moisture-absorption element, and it is therefore highly important that there should be regions where adhesive is present alternating with regions where no adhesive is present, in order to allow unimpeded passage of moisture.

In one attractive embodiment, the adhesive is present in the form of a dot lining pattern. In this case, the dot lining pattern extends over the entire surface of the washable underpad; the pattern is selected in such a manner that there is sufficient free space between the dots of adhesive not to impede passage of moisture.

In a highly attractive embodiment, the pattern of adhesive is composed of separate pattern parts which are separated by regions where there is no adhesive. Of course, a very wide range of types of pattern may be used, but it is advantageous for there to be a number of pattern parts which are identical in shape together with one or more pattern parts of a different shape.

In a highly advantageous embodiment, a pattern part of a different shape is a rectangular border, the external dimensions of which correspond to the dimensions of the washable underpad. The rectangular border, which is therefore present in the interfacial region between top layer material and moisture-absorption element and in the interfacial region between moisture-impermeable bottom layer material and the absorption element, ensures excellent bonding in the border region of the underpad, while inside the rectangular border there may be carefully selected different pattern parts which are responsible for bonding between the three layers in that region.

When selecting the shape of the other pattern parts, it is important that the pattern parts be selected in such a manner that no wrinkling occurs in the underpad, which can give rise to skin problems for the patient/user. The pattern parts may, for example, be circles with a diameter of between 3 and 50 mm; pattern parts with a diameter of 5 mm have given good results. The centre-to-centre distance of the pattern parts may be from 10 to 100 mm, preferably 10 to 60 mm, more preferably 10 to 25 mm. In addition to circles, it is, of course, also possible to use other shapes of pattern parts in the region inside the rectangle, such as for example a spiral structure.

If in particular the top layer material is selected appropriately, in a highly advantageous embodiment there is no need for a finishing edge. In particular if the top layer material is a knitted fabric, in which special measures are taken to prevent fraying, there is no need to apply a separate finishing edge.

In one attractive embodiment, each of the pattern parts is composed of a collection of separate dots. As has been stated above, it is important to ensure unimpeded passage of moisture from the top layer material to the absorption element; forming any pattern parts from dots prevents the passage of moisture from the top layer material to the absorption element from being impeded.

Numerous types of adhesives can be used in the underpad as described above. Firstly, mention may be made of crosslinking adhesives which after application cure over the course of a certain time, if appropriate with heat being supplied.

Examples which may be mentioned include epoxy resin/hardener compositions; polyester resin/hardener compositions and moisture-curable polyurethane or cyanoacrylate compositions.

It is also possible to use thermoplastics which are applied to one material in the molten state, with the material then being brought into contact with another material before the thermoplastic has set as a result of cooling, and with the assembly formed then being allowed to cool until the thermoplastic sets. This process is repeated for the addition of further layers.

Suitable thermoplastics include polyvinyl chloride, polyethylene, polypropylene, polyurethane and the like.

It is also possible to use ethylene vinyl acetate; copolyamide, copolyester.

Examples of suitable thermoplastics which may be mentioned include copolyester No. 1655 produced by EMS-Chemie with a melting point of 188° C. and Unex 1426 produced by Dakota, with a melting point of 140° C.

The Applicant has carried out extensive research into adhesives which can be used, and it has been found that excellent results in terms of the durability of the bonding during washing, during treatment in an autoclave and over the course of time are obtained if the adhesive is selected from a fully moisture-cured reactive hotmelt adhesive, such as a fully moisture-cured reactive polyurethane hotmelt adhesive and a fully moisture-cured reactive polyalkene hotmelt adhesive. Reactive hotmelt adhesives of this type are known, and of these the fully moisture-cured reactive polyurethane hotmelt adhesive is preferred.

A polyurethane hotmelt adhesive which reacts with moisture is formed by reaction of $(HO\text{-}polyol\text{-}OH)_x + (OCN..NCO)_y \rightarrow OCN\text{-}urethane\text{-}NCO$, where y is greater than x. The reactive urethane formed in this way is a thermoplastic material which, when used in air, can be fully cured by water from the air to form a crosslinked polyurethane which is a set material. Full curing can be effected using moisture from the air; of course, it is also possible for full curing to be effected by deliberate addition of water to the reactive thermoplastic urethane material, or water can be supplied, for example, by blowing steam onto the adhesive material. The reactive materials can be obtained from a wide range of sources. Mention may be made, for example, of HPUX9717 from Forbo Swift Adhesives SA of Blois, France and JOWATHERM 603.78 produced by JOWAT KLEBSTOFFE of Detmold, Germany, both products which are examples of reactive polyurethane hotmelt adhesives.

HPUX9717 from Forbo Swift can be applied at a temperature of from 100 to 120° C.; the product is workable in air for from 1 to 5 min and even after 30 s has attained a green strength which allows it to be handled. The curing time is 24 h at a relative humidity of 75%.

JOWATHERM Reaktant 603.78 has a processing temperature of approximately 140° C. and a reaction time of approximately three days, depending on the ambient conditions.

Other suitable types of material include HPUX 9833 and HPUX 9946 produced by Forbo Swift.

Further suitable JOWATHERM grades include 603.00; 603.01; 603.07; 603.08 and 603.09.

In the text which follows, the multilayer washable material is always assumed to be composed of three layers, namely a moisture-permeable top layer material, a moisture-absorption element and a moisture-impermeable bottom layer material.

For certain applications, it may be expedient for additional layers to be present in addition to the said three layers and for the washable underpad as described above also to comprise one or more additional layers of material selected from an anti-allergy layer, a resilient foam layer, a dispersion layer, a bedsore-inhibiting layer and an anti-odour layer, which are bonded to the absorption element and the top layer material or the bottom layer material. Depending on the patient, it is possible, by selecting the additional layer or layers of material, to provide optimum comfort for the patient while he is bedridden.

The invention also relates to a method for producing a multilayer-washable material which comprises at least one layer of a textile material, at least comprising a top layer material, a bottom layer material and an interlayer material positioned between them, wherein a top layer material, a bottom layer material and an interlayer material are provided and are joined to one another using an adhesive composition, which is characterized in that an adhesive composition is applied in the form of a pattern which prevents wrinkling both in the interfacial region which is to be formed between top layer material and interlayer material and in the interfacial region which is to be formed between bottom layer material and interlayer material, and the layers are brought to bear against one another and are joined to one another as the adhesive composition sets, with no finishing of the multilayer material as such and/or a smaller part which is cut from it, being carried out.

Attractive embodiments of the above method are described in dependent claims 9-14, which will be explained in more detail in the text which follows.

Depending on the type of method which is carried out, the layers of material to be used in the method may be in sheet or web form. The sheet form is generally used in discontinuous processes, whereas the web form is preferred for continuous processes.

In one particular embodiment, the method according to the invention relates to the production of a washable underpad at least comprising a moisture-permeable top layer material, a moisture-impermeable bottom layer material and a moisture-absorption element positioned between them, wherein a moisture-permeable top layer material, a moisture-impermeable bottom layer material and a moisture-absorption element are provided and are joined to one another.

According to the invention, an adhesive composition is applied both in the interfacial region which is to be formed between top layer material and moisture-absorption element and in the interfacial region which is to be formed between bottom layer material and moisture-absorption element, after which the layers are brought to bear against one another and are joined to one another.

The adhesive composition can be applied in various ways, among which spraying, lamination, application using a slot coater and printing may be mentioned as attractive embodiments. In the case of lamination, consideration may be given to a layer of adhesive which is incorporated between two layers of release material; removing one of the layers of release material makes it possible for the adhesive material to be stuck to one layer selected from the top layer material and the bottom layer material; removing the second layer of release material enables the top layer material or bottom layer material which has been provided with adhesive in this way to be stuck to the moisture-absorption element. This operation is repeated in order to form the washable underpad comprising three layers.

In the case of application by printing, mentioned may be made of intaglio printing and screen printing, although the invention is not restricted to these two specific methods. In the case of intaglio printing, adhesive is applied with the aid of a roller which includes indentations, with applications of up to 25 g/m$^2$ being readily possible in general.

Higher levels of application can be realized by screen printing, in flat-bed or rotary form.

If the adhesive composition is sprayed, the adhesive composition is generally applied to the top layer material and the bottom layer material, after which the said layers are joined to the moisture-absorption element under pressure. The adhesive composition to be used in the method according to the invention is selected from a nonreactive thermoplastic material which is solid under ambient conditions and a moisture-curable plastic material, while it is applied in the form of a melt at a temperature higher than the melting point of the plastic material used.

The adhesive composition is expediently a moisture-curing plastic material, while the application takes place in the form of a melt at a temperature which is higher than the melting point of the plastic material used.

Obviously, the moisture-curing plastic material requires a certain time after application to the various layers and after they have been finally stuck to one another before it is fully cured. During the curing period, the contact between the various layers will be maintained in order to ensure final bonding which is able to withstand handling during subsequent use and washing.

In one attractive embodiment of the method, the moisture-curing plastic material is applied to the top layer material and the bottom layer material. Both the top layer material and the bottom layer material are relatively dense materials which are eminently suitable for receiving a moisture-curing plastic material without loss of significant properties of moisture-curing plastic material occurring as a result of breakthroughs.

Of course, if desired the moisture-curing plastic material can also be applied to both sides of the moisture-absorption element; it should then be ensured, by selection of the application technique, that penetration of the plastic material remains limited to the surface layers on both sides of the moisture-absorption element.

Application of the molten moisture-curing plastic material by printing can be executed in various ways; mention may be made of intaglio printing and screen printing.

In one attractive embodiment, the molten moisture-curing plastic material is applied with the aid of screen printing, in which case at least the screen-printing stencil used is heated to above the melting point of the moisture-curing plastic used.

Obviously, in addition to the screen-printing stencil which is heated to above the melting point of the moisture-curing plastic used, it is also possible for the moisture-curing plastic material itself and/or the squeegee used to be heated in order to ensure that there is no premature solidification of the moisture-curing plastic material in the stencil.

Screen printing can be carried out in various ways.

With flat-bed screen printing, in which the stencil is a flat frame with a (metal) gauze tensioned inside it, it is possible to provide web-like materials with a printed pattern; it is also possible for separate parts of the material (for example of the size of the washable underpad) to be printed with a pattern of adhesive composition. It is also possible for rotary screen printing to be used in an extremely attractive embodiment of the method according to the invention, in which case it is possible to employ one or more seamless cylindrical metal stencils. In rotary screen printing, a seamless, cylindrical metal stencil is brought into rotary contact with, for example, an endless belt, with the material which is to be provided with a pattern or is to be printed while it rests on the endless belt by means of the rotating stencil. In this case, therefore, the printed pattern comprises a molten moisture-curing plastic material. The rotary screen-printing stencils used may be of various types and structures; Stork Prints of Boxmeer (NL) supplies stencils of this type, as well as devices in which stencils of this type can be used. Stencils can be obtained in a wide range of finenesses, thicknesses and diameters; a stencil used in the method described here was denoted CP52-12-200, where CP52 stands for 52 holes per cm$^2$. The open percentage of a stencil of this type is 12%, and the wall thickness of the stencil is 200 μm. Another type of stencil which gave good results is CP52-18-200.

The moisture-curing plastic material used is preferably selected from a reactive polyurethane hotmelt adhesive and a reactive polyalkene hotmelt adhesive; of these, the reactive polyurethane hotmelt adhesive is preferred.

As has been described above, a number of materials of this type are commercially available; good results have been obtained using HPUX9717 produced by Forbo Swift of Blois, France and JOWATHERM REAKTANT PUR-Hotmelt 603.78 produced by JOWAT KLEBESTOFFE of Detmold, Germany.

The method in accordance with the embodiment described above using rotary screen printing can be carried out in various ways.

For example, in a one-head machine, that side of the top layer which faces the moisture-absorption element can first of all be provided with an adhesive material, after which the absorption element is laminated onto it. As the second step, the adhesive material is applied to that side of the bottom layer material which, in the washable underpad, bears against the other side of the absorption element, after which the assembly formed in the first step is laid against that side of the bottom layer material which has been coated with the adhesive material. Steps one and two are carried out separately and in succession using a machine with one printing station.

In general, to form washable multilayer material, such as for example material for washable underpads, rotary screen printing is used to apply a pattern of a moisture-curable plastic material to a moisture-permeable top layer material and to a moisture-impermeable bottom layer material, and the materials which have been coated in this way are combined with a moisture-absorption element, in such a manner that those sides of the top layer material and the bottom layer material which contain the moisture-curable plastic material come to bear against the two surfaces of the moisture-absorption element, and curing of the moisture-curable plastic material bonds together the top layer material, bottom layer material and moisture-absorption element.

The above text has described the application of the adhesive to the top layer material and the bottom layer material and the joining of these materials to the moisture-absorption element.

Obviously, if desired, it is also possible for the adhesive to be applied by printing to the two flat sides of the moisture-absorption element, after which the moisture-absorption element is brought to bear against the top layer material and the bottom layer material in order to form a washable underpad. In this case, the printing of the moisture-absorption element and the combining of this element with the top layer and bottom layer material can be carried out in a single operation; it is also possible to carry out separate operations of printing the moisture-absorption element and bringing it to bear against, for example, the top layer material and then printing the other side of the moisture-absorption element and bringing it to bear against the bottom layer material.

The general method referred to above can be carried out using both a single-head rotary screen-printing device and a two-head rotary screen-printing device.

However, it is expedient for the top layer material and the bottom layer material to be in web form, while moisture-curable plastic material is applied to both materials simultaneously with the aid of two rotary screen-printing stencils, and the top layer and bottom layer materials which have been coated in this way are brought to bear against a moisture-absorption element in web form, after which moisture-curing of the curable plastic material bonds together the top layer material, bottom layer material and moisture-absorption element.

It is preferable for a method of this type as described above to be carried out continuously, while after an assembly of top layer material, bottom layer material, and moisture-absorption element in web form has been formed, this web is divided by cutting into separate, washable underpads which, if necessary, are provided with an edge finishing. In the continuous embodiment outlined above, the adhesive composition used will preferably be a quick-curing adhesive composition, such as a moisture-curing adhesive composition.

Of course, the moisture-curable plastic material as described above requires moisture in order to acquire the correct strength through full curing. The moisture required can be provided by the atmospheric humidity which is normally present; in areas of low atmospheric humidity and/or during times where the atmospheric humidity is low, it may be advantageous to accelerate and/or ensure full curing by the application of moisture while the method is being carried out.

Therefore, in an advantageous embodiment, to fully cure the moisture-curable plastic material, moisture is supplied in an amount which is sufficient to enable the moisture-curable plastic material on the top layer material and bottom layer material to cure fully. The moisture used may be liquid, in the form of atomized water; it is also possible to use steam.

The latter form is preferred, since this prevents premature solidification of the molten moisture-curable plastic material which is thermoplastic during application.

It is preferable for the moisture-curable plastic material to be applied in pattern form to the top layer material and the bottom layer material.

The pattern shape is selected to be such that wrinkling of the washable multilayer material, such as a washable underpad, is prevented in use, and is expediently selected from:
a) a dot lining pattern,
b) separately positioned pattern parts which are separated by regions where there is no adhesive composition,
c) a number of pattern parts which are identical in shape and one or more pattern parts of a different shape,
d) the patterns described under b) and/or c), with one or more pattern parts being formed from a dot lining pattern,
e) a dot lining pattern as described under a) in which there are parts without any dots,
and combinations of the patterns described under a) to e).

A pattern of this type is expediently divided into pattern parts, in which case it is advantageous for one pattern part to comprise at least one rectangle with dimensions which correspond to the dimensions of the finished washable underpad. In this context, the term rectangle is to be understood as meaning a pure geometric rectangle, as well as shapes which deviate slightly therefrom. An example of a slightly deviating shape may have rounded corners or scalloped or slightly rounded sides. In a further attractive embodiment, two sides of the rectangle of the rectangular pattern part lie at the edge of the top layer and bottom layer materials in web form; the other two sides of the rectangle in this case extend across the width of the top layer and bottom layer materials in web form.

As has been discussed above, in addition to the rectangle there are also parts in pattern form which are located inside this rectangle. As has been stated above, these additional parts in pattern form may adopt all kinds of shapes and densities per unit area; the shape and density are determined by the desire to prevent wrinkling in the washable underpad and as far as possible to promote passage of moisture at least from the top layer material to the absorption element.

Incorporating additional pattern parts inside the rectangle provides the option of forming air pockets which are distributed over the underpad. These air pockets are of benefit to the patient's comfort and are favourable to the drying characteristics after washing. One example of a shape of this type is a full-area dot lining, in which, however, round parts with a diameter of 5 mm and a centre-to-centre distance of 16 mm arranged in an equilateral triangle are left clear of the dot lining. A pattern of this type has proven eminently suitable for the prevention of wrinkling yet at the same time the material has retained an extremely comfortable flexibility.

The abovementioned pattern parts, such as the rectangle and additional pattern parts, are expediently divided into dots.

Obviously, it is also possible for the entire pattern to be composed of dots and to extend over the entire surface of the top layer material and the bottom layer material, while otherwise, as stated above, it is possible for the pattern parts to be composed of dots.

Forming all the pattern parts from dots creates very great flexibility for the material of the washable underpad.

Even if the top layer and moisture-absorption element and bottom layer and moisture-absorption element are joined over their entire surface by means of dot lining layers, excellent flexibility is obtained, which is to the benefit of the patient's comfort.

During washing, the washable multilayer material, on account of the form of joining by means of the selected pattern and dot structure selected, will undergo controlled shrinkage which does not manifest itself in the form of wrinkling. The materials can shrink automatically, while differences in shrinkage between the layers are absorbed as a result of the particular structure and are distributed throughout the entire surface. After an assembly in web form which is composed of top layer material, bottom layer material and moisture-absorption element has been formed, the assembly formed in this way is divided into washable underpads, during which process, given an appropriate selection in terms of materials and pattern of adhesive composition, there is no need to apply a separate finishing edge.

Of course, the washable underpad material in web form, after it has been formed, can also be rolled up and supplied in this form, in which case the recipient is responsible for cutting and any finishing.

To allow the washable underpad to be matched to the patient's requirements, it is also possible for one or more additional layers of material, such as an anti-allergy layer, a resilient foam layer, a dispersion layer and a bedsore-inhibiting layer, to be applied, which layers are bonded to the moisture-absorption element and the top layer material or the bottom layer material. On the other hand, it is also possible to add an anti-odour layer, such as a fibre layer which contains activated carbon and is assembled in the same way as the moisture-absorption element. The activated carbon may also, optionally locally, be incorporated in the moisture-absorption element.

The quantity of adhesive composition, for example a moisture-curable polyurethane hotmelt adhesive as described above, to be applied is from 6 to 40 $g/m^2$, expediently from 10 to 30 $g/m^2$. For an absorption-element quality of 150 $g/m^2$ as standard and 450 $g/m^2$ for additional absorption capacity, in general a minimum quantity of adhesive composition of 15 $g/m^2$ will be required. For the application of additional water, in general 3 to 4 ml per $m^2$ would be sufficient in order to bring about the reaction; at atmospheric humidity of RH 50% and above, there is generally no need to apply water unless it is desired to increase the reaction rate. Extra water should in general be applied if the atmospheric humidity is lower than 50% RH.

The abovementioned weight range for the moisture-absorption element applies in particular to multilayer materials of the incontinence underpad type. For other applications, different weights will be used: for pantyliner materials 200-800 $g/m^2$; for sanitary towels 50-250 $g/m^2$, etc.

With the abovementioned stencil type CP52-12-200, the open percentage of the stencil is approximately 12%; liquefying the adhesive gives a surface coverage of 15%. The openings in the stencil are approximately 540 µm; flow produces a curable plastic dot of 604 µm. The centre-to-centre distance of the dots is approximately 1540 µm when using the abovementioned stencil; the distance between the dots is then approximately 936 µm.

The invention will now be explained with reference to the drawing, in which.

Figure 1:
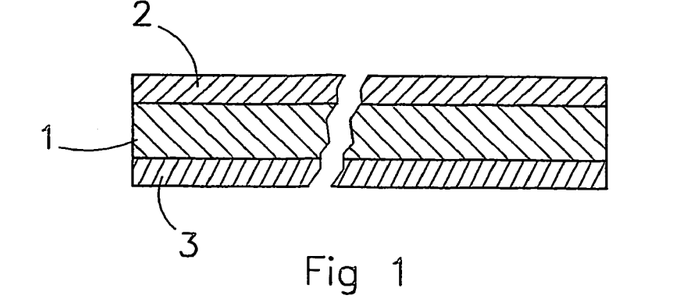
FIG. 1 diagrammatically depicts a washable underpad.

In FIG. 1, a moisture-absorption element is denoted by 1, a moisture-permeable top layer material is denoted by 2 and a moisture-impermeable bottom layer material is denoted by 3. The materials 1, 2 and 3 are stuck together with the aid of an adhesive composition, such as a moisture-cured, reactive polyurethane hotmelt material. The three layers are of equal size, and by suitable selection of the pattern of adhesive it was possible to obviate the need for edge finishing.

Figure 2:
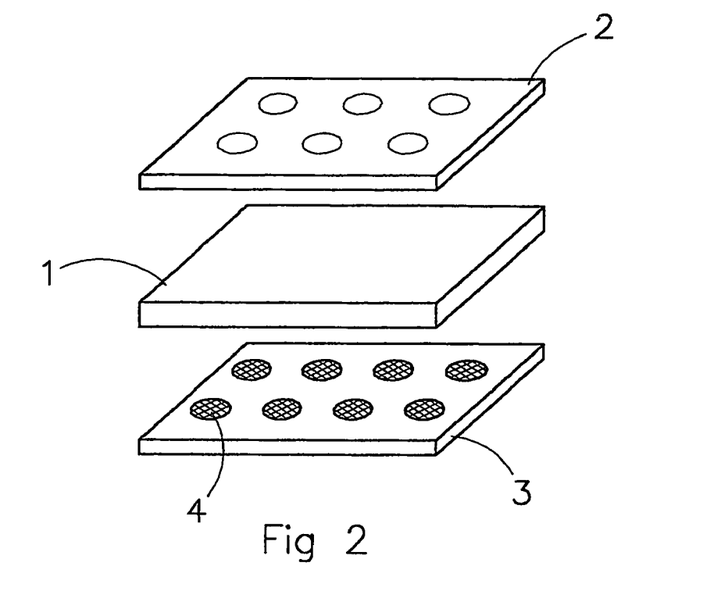
FIG. 2 shows the structure of a washable underpad of this type illustrating its individual components.

FIG. 2 shows the same layers 1, 2 and 3 in a situation in which they are not yet joined. Dots of an adhesive composition have been applied to that side of the top layer material 2 which faces the absorption element 1; dots of an adhesive composition, which are denoted by 4, have also been applied to that side of the moisture-impermeable bottom layer material 3 which faces the absorption element. The dots indicated here are relatively large dots, which may optionally be subdivided into smaller dots as discussed above. To complete assembly, the layers 1, 2 and 3 are brought to bear against one another and the adhesive composition dots are allowed to cure fully, under gentle pressure, so that the three layers are bonded together.

Figure 3:
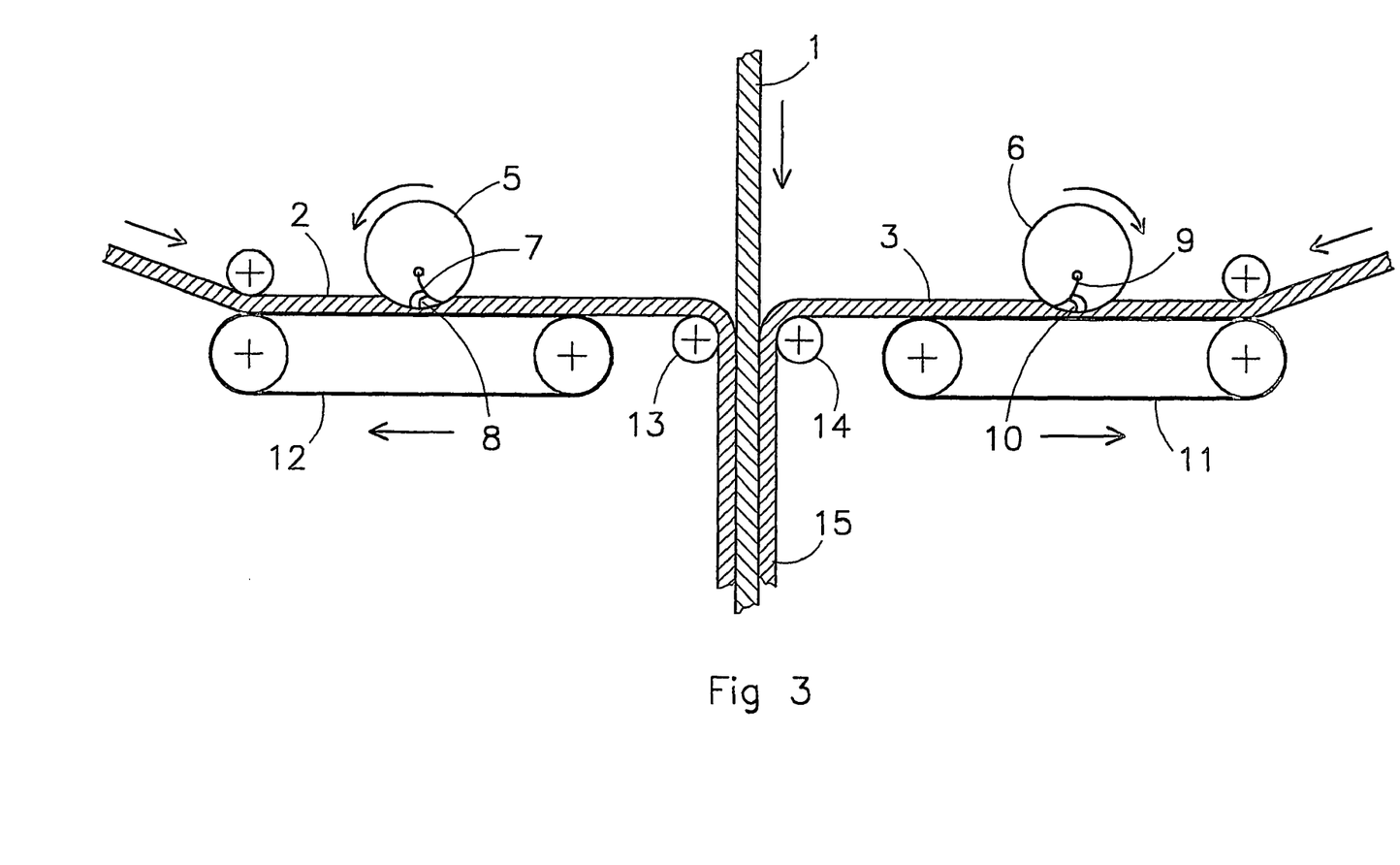
FIG. 3 diagrammatically depicts a method carried out using a machine with two heads.

FIG. 3 shows that a moisture-absorption element 1 is covered on its two sides by a moisture-permeable top layer material 2 and a moisture-impermeable bottom layer material 3, respectively. The top layer material is coated with adhesive composition 8 with the aid of a rotary screen-printing stencil 5 via the intervention of a squeegee 7; to this end, the moisture-permeable top layer material is supplied continuously from a reel (not shown) and is brought to bear against an endless belt 12.

The same operation is carried out on the moisture-impermeable bottom layer material 3, which is supplied continuously and with the aid of a rotary screen-printing stencil 6 is coated with adhesive composition 10 in pattern form via the intervention of a squeegee 9. The moisture-impermeable bottom layer material is supplied and placed onto an endless belt 11. After the adhesive composition 8 and 10 has been applied, the top layer material and the bottom layer material are brought to bear against the moisture-absorption element using rollers 13 and 14, in order to form an assembly comprising top layer material, bottom layer material and moisture-absorption element 15.

The assembly 15 formed in this way is generally rolled up to form a reel, after which the material is left to stand for 1 to 5 days in order to allow the moisture-curable adhesive composition to fully cure.

Obviously, as has been discussed, it is also possible for moisture to be applied or steam supplied in the area between the rotary screen-printing stencils 5 and 6 and the rollers 13 and 14, in order to promote full curing of the adhesive composition or simply to enable the adhesive composition to cure fully if the atmospheric humidity is particularly low.

During the coating of the top layer material 2 and bottom layer material 3, the stencil 5, 6 used and possibly also the squeegee 7, 9 and the adhesive composition 8, 10 will expediently be heated, so that the adhesive composition becomes a (viscous) liquid and can be applied to the materials by printing.

It is generally not necessary to heat the materials 2, 3 and 1, and consequently the thermal load on these materials is limited to the heat content of the adhesive composition applied.

In very exceptional circumstances, it is possible to decide to heat one or more of the materials 2, 3 or 1; even then, it is possible to limit the heating to a temperature which keeps the applied hot molten adhesive composition in liquid form for sufficient time.

The description given above on the basis of FIG. 3 has assumed that top layer material 2, bottom layer material 3 and moisture-absorption element 1 are of the same width. In one attractive variant, the width of the absorption element 1 is less than that of the top layer material 2 and the bottom layer material 3, which are of the same width. It is also possible for the narrower web of the absorption element 1 to be divided into a plurality of webs of even smaller width. The pressure-exerting rollers 13, 14 can be matched to this division in a customary way or divided into a plurality of rollers over the overall width taking the division into account.

The advantage of a multilayer material formed in this way is that its edges or the edges of the parts formed after division have a thinner edge, facilitating its use. This embodiment also reduces the consumption of raw materials.

Figure 4:
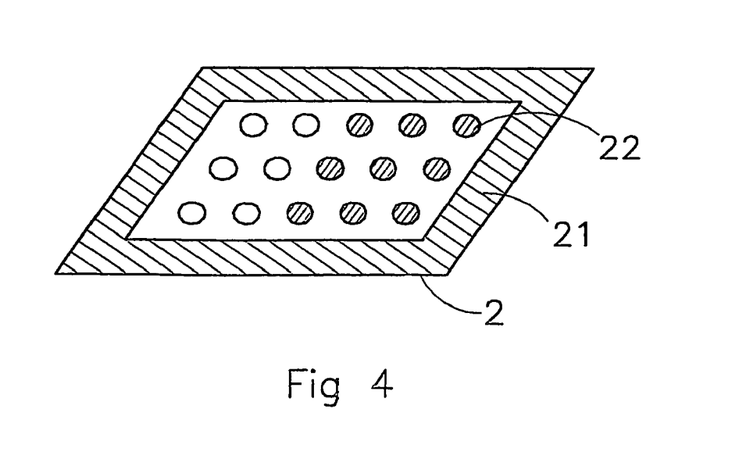
FIG. 4 shows a top layer material which is provided with a pattern of an adhesive composition.

FIG. 4 diagrammatically depicts an adhesive material coating in pattern form, in this case on that side of the top layer material which is to face the moisture-absorption element. The pattern comprises a rectangular border 21 and deviating pattern parts 22. The pattern parts 21 and 22 may be printed over the entire surface; of course, as has been discussed earlier, they may also take the form of a dot lining, i.e. the pattern parts 21 and 22 shown can be divided into a large number of small dots which are isolated from one another. Obviously, it is also possible for the abovementioned dot lining in turn to be applied in pattern form, i.e. for the dots within the pattern parts 21 and 22 in turn to be arranged in pattern form.

With regard to the stability of the washable multilayer material from which, for example, a washable underpad is formed, in accordance with the invention having a top layer material, moisture-absorption element and bottom layer material as described and a moisture-cured plastic material, such as a reactive polyurethane hotmelt (HPUX9717; Forbo Swift), it should be noted that the adhesive is able to withstand a treatment for 12 hours in an autoclave (126° C.; 1.45 bar) with 90% of the original tensile strength of the polymer being retained. An underpad which is formed in the manner described above can withstand from 150 to 200 or more washes.

Figure 5:
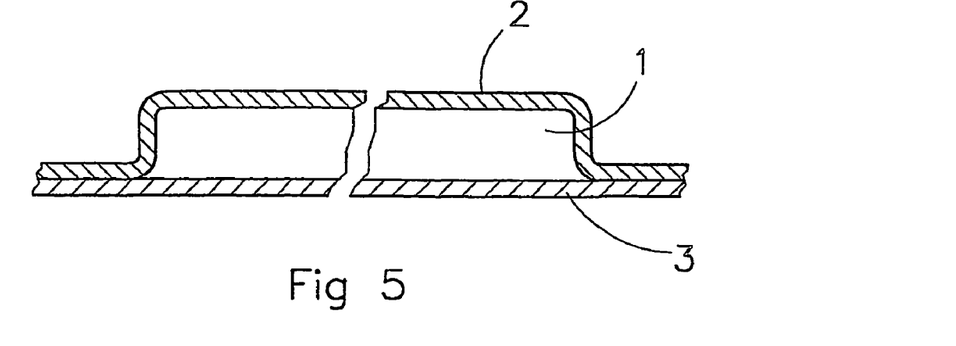
FIGS. 5-10 show various embodiments of the structure and edge finishing of an underpad according to the invention.

In FIG. 5, the top layer 2 is joined via hotmelt dots to layer 1, which is narrower, and the assembly of 1 and 2 is joined to the moisture-impermeable layer 3. This produces a finishing, eliminating the need for fully made-up finishing.

Figure 6:
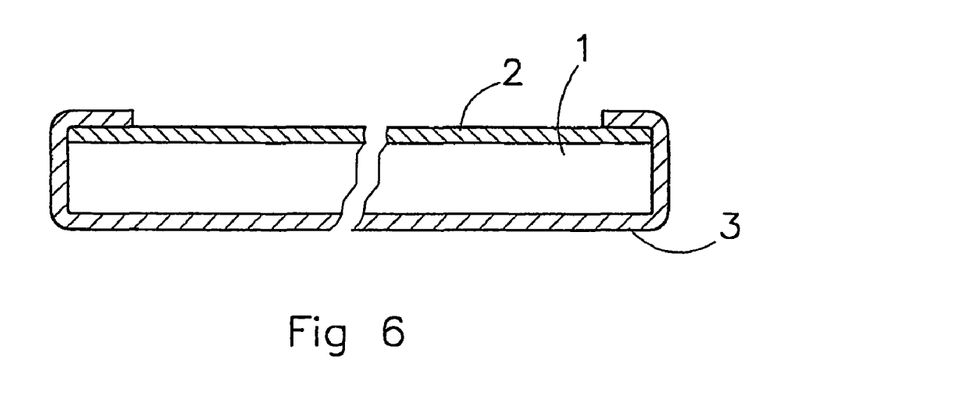

In FIG. 6, top layer 2 and moisture-absorbent layer 1 are of the same width and are joined to one another over their length by means of hotmelt dots. The assembly of 1 and 2 is joined to layer 3, the width of which is greater. Layer 3 is fixed onto the top edge of layer 2 by being folded over it.

Figure 7:
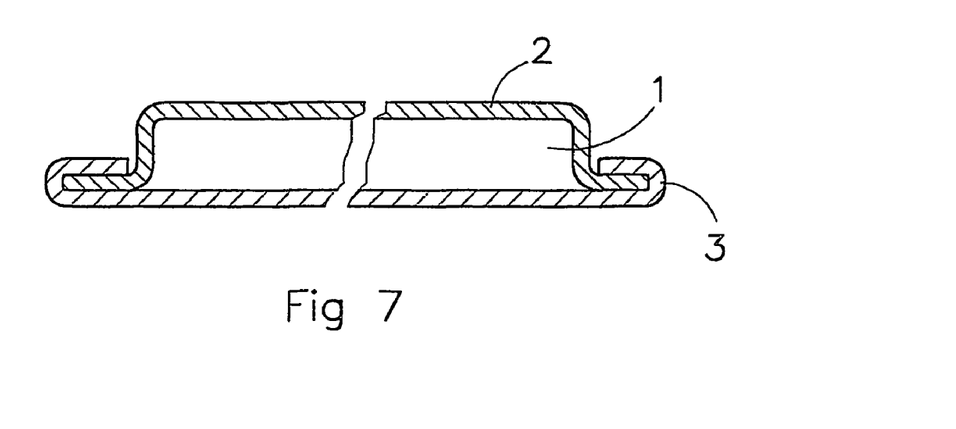

In FIG. 7, the wider top layer 2 is joined to the narrower moisture-absorbent layer 1. The moisture-impermeable layer 3 is joined to the assembly of 1 and 2 and folded over onto the moisture-permeable top layer 2 which projects beyond layer 1.

Figure 8:
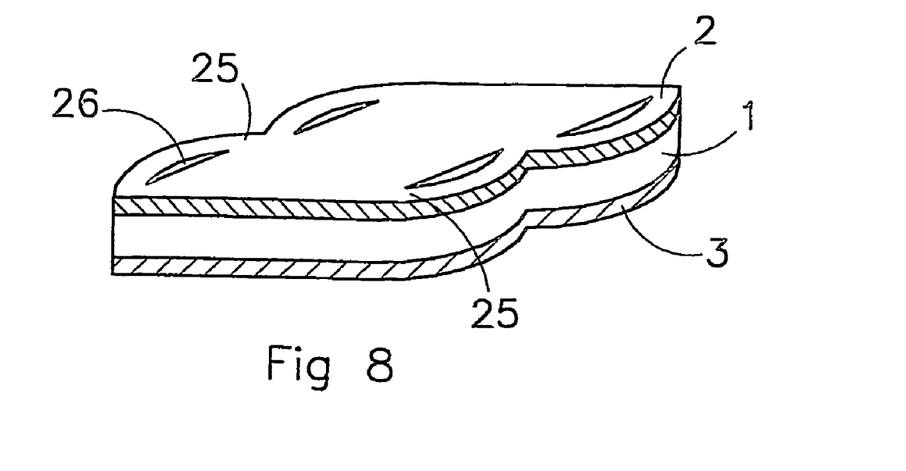

FIG. 8 shows an embodiment with handles. In this case, after the three-layer assembly has been produced, stamping is used to form an assembly in which both sides of the underpad have been stamped into the shape of two semi-ovals 25 in the longitudinal direction. Openings 26 which form handles are punched into these shapes.

Figure 9:
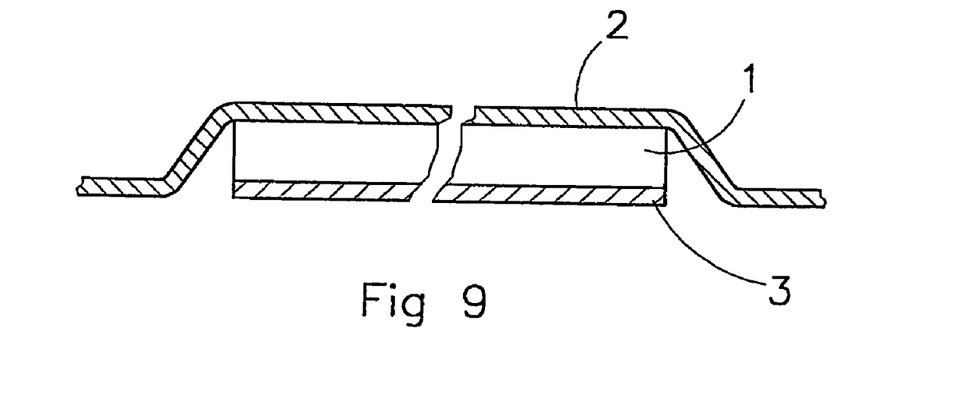

In the embodiment shown in FIG. 9, the top layer 2 is on both sides 30 to 40 cm wider than the absorbent layer 1 and the moisture-impermeable bottom layer 3. This embodiment facilitates fixing the underpad in place by tucking it in.

Figure 10:
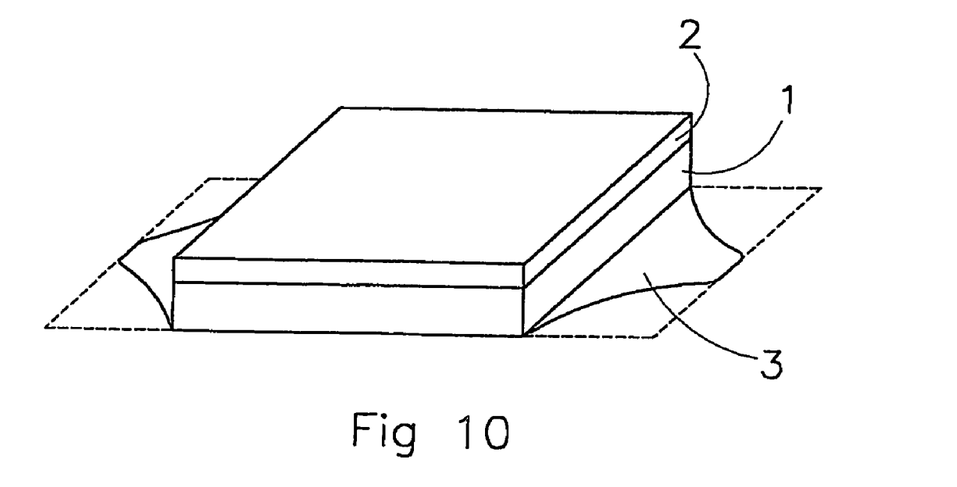

In the embodiment shown in FIG. 10, the moisture-impermeable bottom layer 3 is 30 to 40 cm wider than the top layer 2 and the absorbent layer 1. This too facilitates fixing of the underpad by tucking it in.

Figure 11:
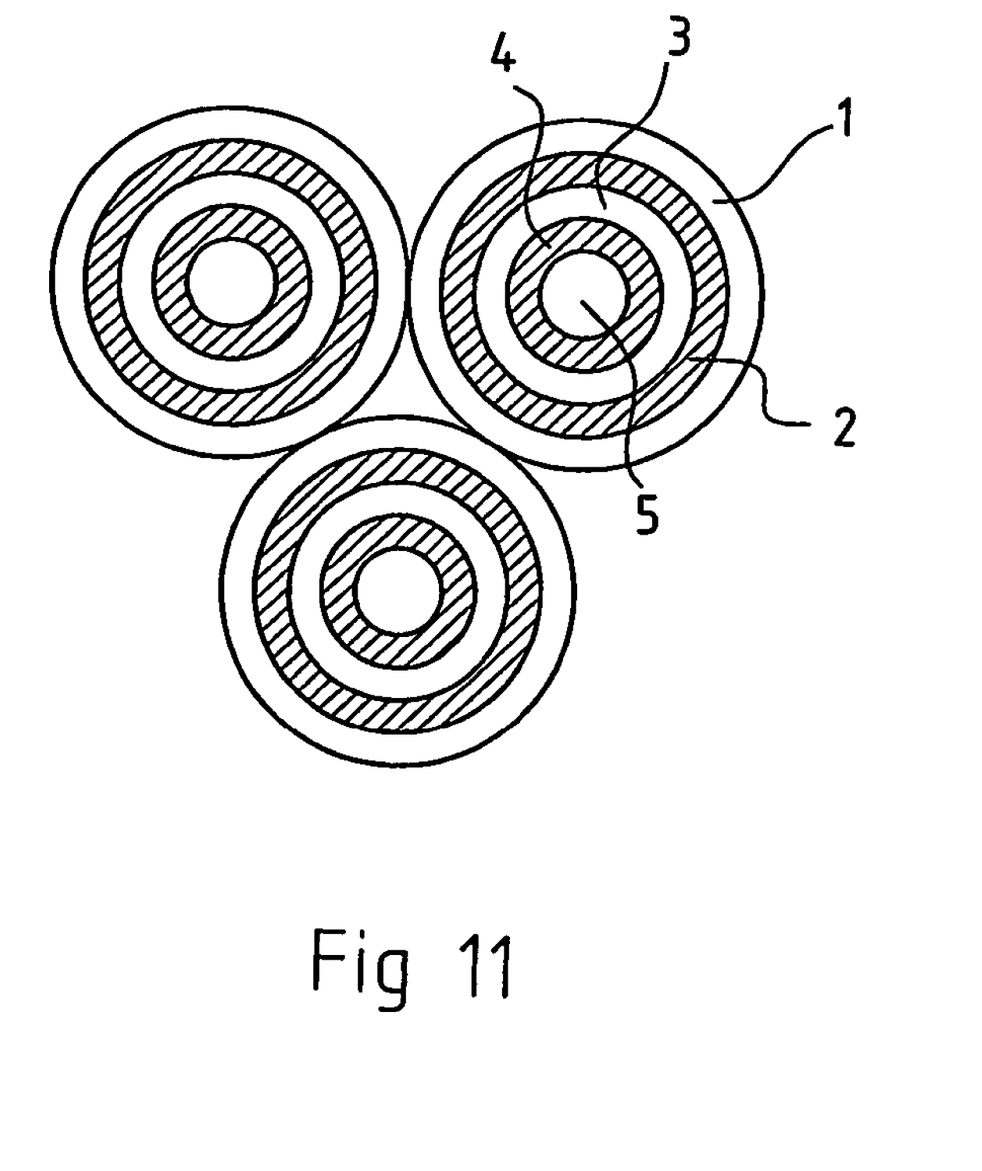
FIG. 11 shows an illustration of a screen-printing stencil for applying a pattern of adhesive composition.

FIG. 11 shows a preferred design of the screen-printing stencil for applying a pattern of adhesive composition in the interface between two layers which bear against one another in the ready-to-use state of a washable multilayer material. Depending on the design aspects, the pattern can be applied to one layer or the other and can function in the interface when the layers are being joined together.

The figure shows a pattern composed of sets of circles, with the centre of each of the three sets lying at a corner of an equilateral triangle.

In the case of a rotary screen-printing stencil of type CP52-18%-200 µm, pattern part 1 has an external diameter of 22 mm and is open, part 2 has an external diameter of 18 mm and is closed, part 3 has an external diameter of 13 mm and is open, part 4 has an external diameter of 9 mm and is closed and pattern part 5 has an external diameter of 4 mm and is open. In this context, the term open means that the holes in the stencil are not covered and allow an adhesive composition to pass through. A pattern part of this type, depending on the form of printing, is a completely continuous pattern part or a pattern part composed of dots. In the latter case, the dimensions of the dots correspond to the dimensions of the holes in the stencil.

As has been indicated above, the term washable underpad encompasses not only the underpad per se, but also the material which can be used for other purposes.

The Applicant has successfully used the material in:
sanitary towels
incontinence products for patients who are not bedridden
anti-leak material at stomas
bibs for babies and adults
medical dressings
operating chamber covering cloths and textiles (sterilizable)
washable diapers
saddlecloths for horses
dog/cat mats
recreational beach mats
car seat mats (to combat perspiration)
disinfecting running mats (optionally sterilizable)
washable sterilizable plasters
dressing material
sleeping mats
filter material
breast compressors
incontinence material for men
doormats
liquid-absorbent mats.

The invention claimed is:

1. A multilayer washable material which comprises:
   a moisture-permeable top layer material (2) being substantially hydrophobic, a moisture-impermeable bottom layer material (3), and at least one layer of a textile material used as a moisture-absorption element (1) positioned between the top layer and the bottom layer;
   the layers being joined to one another by means of an adhesive composition, wherein an interfacial region between each pair of layers bearing against one another exists;
   wherein in the interfacial region between each pair of layers bearing against one another there is an adhesive composition in the form of a pattern which is sufficiently dense to prevent wrinkling, and which is sufficiently open to prevent the material from becoming inflexible;
   wherein the pattern in which the adhesive composition is present is selected from:
   a) a dot lining pattern,
   b) separately positioned pattern parts which are separated by regions where there is no adhesive composition,
   c) a number of pattern parts (4, 22) which are identical in shape and one or more pattern parts (21) of a different shape, wherein the different pattern shape is a border, the external dimensions of which correspond to the dimensions of a use product, which it is desired to form from the multilayer material by dividing up the latter,
   d) the patterns described under b) and/or c), with one or more pattern parts being formed from a dot lining pattern, e) a dot lining pattern as described under a) in which there are parts without any dots,
and combinations of the patterns described under a) to e);

wherein the multilayer material is a washable underpad;

wherein the moisture-permeable top layer is made of a fraying-free fabric;

wherein optionally no finishing of the multilayer material, as such and/or of a smaller part obtained therefrom, is carried out; and wherein a quantity of applied adhesive composition is from 6 to 40 g/m$^2$.

2. The multilayer material according to claim 1, wherein the adhesive composition is selected from solidified, nonreactive thermoplastic material and a fully moisture-cured reactive hotmelt adhesive.

3. The multilayer material according to claim 2, wherein the adhesive composition is a fully moisture-cured reactive polyurethane hotmelt adhesive.

4. The multilayer material according to claim 1, wherein the multilayer material comprises one or more additional layers of material selected from an anti-allergy layer, a resilient foam layer, a dispersion layer, an anti-bedsore layer and an anti-odour layer, which are bonded to the moisture-absorption element (1) and the top layer material (2) or the bottom layer material (3).

5. The multilayer material according to claim 1, wherein the moisture-permeable top layer material comprises a knitted polyester material comprising approximately 85% polyester fibers, and wherein the moisture-impermeable bottom layer material comprises PVC.

6. The multilayer material according to claim 5, wherein the quantity of applied adhesive composition is approximately 15 g/m$^2$.

7. A method for producing a multilayer washable material which comprises a moisture-permeable top layer material (2) being substantially hydrophobic, a moisture-impermeable bottom layer material (3) and at least one layer of a textile material used as a moisture-absorption element (1) positioned between them, wherein the top layer material (2), the bottom layer material (3) and the moisture-absorption element (1) are provided and are joined to one another using an adhesive composition, wherein an interfacial region between each pair of layers bearing against one another is formed, wherein an adhesive composition is applied in a quantity of from 6 to 40 g/m$^2$ in the form of a pattern which prevents wrinkling and which is sufficiently open to prevent the material from becoming inflexible both in the interfacial region which is to be formed between top layer material (2) and the moisture-absorption element (1) and in the interfacial region which is to be formed between bottom layer material (3) and the moisture-absorption element (1), and the layers are brought to bear against one another and are joined to one another as the adhesive composition sets, and wherein the multilayer material is a washable underpad, the pattern in which the adhesive composition is applied is selected from:

a) a dot lining pattern, b) separately positioned pattern parts which are separated by regions where there is no adhesive composition, c) a number of pattern parts (4, 22) which are identical in shape and one or more pattern parts (21) of a different shape, wherein the different pattern shape is a border, the external dimensions of which correspond to the dimensions of a use product, which it is desired to form from the multilayer material by dividing up the latter, d) the patterns described under b and/or c), with one or more pattern parts being formed from a dot lining pattern, e) a dot lining pattern as described under a) in which there are parts without any dots,
and combinations of the patterns described under a) to e).

8. The method according to claim 7, wherein the adhesive composition is selected from a nonreactive thermoplastic material which is solid under ambient conditions and a moisture-curable plastic material, and it is applied in the form of a melt at a temperature which is higher than the melting point of the plastic material used.

9. The method according to claim 8, wherein a moisture-curable plastic material is applied to the top layer material (2) and the bottom layer material (3).

10. The method according to claim 9, wherein a molten moisture-curable plastic material is applied with the aid of screen printing, with at least the stencil used being heated to above the melting point of the moisture-curable plastic material used.

11. The method according to claim 10, wherein the screen printing used is rotary screen printing using one or more seamless cylindrical metal stencils (5, 6).

12. The method according to claim 8, wherein the moisture-curable plastic material used is a plastic material selected from a reactive polyurethane hotmelt adhesive and a reactive polyalkene hotmelt adhesive.

13. The method according to claim 12, wherein a reactive polyurethane hotmelt adhesive is used.

14. The method according to claim 7, wherein to form a multilayer material in the form of a washable underpad with the aid of rotary screen printing, a pattern of a moisture-curable plastic material is applied to the moisture-permeable top layer material (2) and to the moisture-impermeable bottom layer material (3), and the materials which have been coated in this way are combined with the moisture-absorption element (1) in such a manner that the sides of the top layer material (2) and the bottom layer material (3) which comprise moisture-curable plastic material bear against the two surfaces of the moisture-absorption element (1), and curing of the moisture-curable plastic material bonds together the top layer material (2), bottom layer material (3) and the moisture-absorption element.

15. The method according to claim 14, wherein the top layer material (2) and the bottom layer material (3) are in web form, and moisture-curable plastic material (7, 9) is applied to both materials simultaneously with the aid of two rotary screen-printing stencils (5, 6), and the top layer and bottom layer materials which have been coated in this way are brought to bear against a moisture-absorption element in web form, after which moisture-curing of the moisture-curable plastic material bonds together the top layer material (2), bottom layer material (3), and moisture-absorption element (1).

16. The method according to claim 15, wherein it is carried out continuously, and after an assembly of top layer material (2), bottom layer material (3) and moisture-absorption element (1) in web form has been formed, the web is divided into separate, washable underpads by cutting, and these underpads are used with the need for separate edge finishing being obviated.

17. The method according to claim 14, wherein one or more additional layers of material selected from an anti-allergy layer, a resilient foam layer, a dispersion layer, a bedsore-inhibiting layer and an anti-odour layer are applied and these layers are bonded to the absorption element (1) and the top layer material (2) or the bottom layer material (3).

18. The method according to claim 7, wherein to fully cure the moisture-curable plastic, moisture is supplied in an amount sufficient to enable the moisture-curable plastic on the top layer material (2) and bottom layer material (3) to cure fully.

19. The method according to claim 14, wherein the pattern on the top layer material (2) and the bottom layer material (3) extends over the entire surface thereof and comprises dots, or the pattern parts (4, 21, 22) are composed of dots.

20. The method according to claim 7, wherein the moisture-permeable top layer material comprises a knitted polyester material comprising approximately 85% polyester fibers, and wherein the moisture-impermeable bottom layer material comprises PVC.

21. The method according to claim 20, wherein the quantity of applied adhesive composition is approximately 15 g/m$^2$.

* * * * *